(12) United States Patent
Russell et al.

(10) Patent No.: US 8,400,302 B2
(45) Date of Patent: Mar. 19, 2013

(54) ELECTRIC FIELD SENSING DEVICE

(75) Inventors: Brian Keith Russell, Auckland (NZ);
Paul Benjamin Mallinson, Auckland (NZ); Stephen Christopher Kent, Auckland (NZ); Christopher Michael Solomon, Auckland (NZ)

(73) Assignee: Zephyr Technology Corporation, Annapolis, MD (US)

( * ) Notice: Subject to any disclaimer, the term of this patent is extended or adjusted under 35 U.S.C. 154(b) by 0 days.

(21) Appl. No.: 12/813,374

(22) Filed: Jun. 10, 2010

(65) Prior Publication Data

US 2011/0133931 A1 Jun. 9, 2011

Related U.S. Application Data

(63) Continuation of application No. 11/791,208, filed as application No. PCT/NZ2005/000309 on Nov. 22, 2005, now abandoned.

(30) Foreign Application Priority Data

Nov. 22, 2004 (NZ) ........................................ 536762

(51) Int. Cl.
*G08B 13/26* (2006.01)
(52) U.S. Cl. ..................... 340/561; 340/573.1; 340/665; 600/587
(58) Field of Classification Search .................. 340/561, 340/573.1, 665–667, 539.1, 539.12, 539.13; 324/600, 635, 644, 662, 671, 699; 600/587, 600/592, 595, 534
See application file for complete search history.

(56) References Cited

U.S. PATENT DOCUMENTS

| 4,033,332 | A | 7/1977 | Hardway, Jr. ..................... 128/2 |
| 4,931,740 | A | 6/1990 | Hassanzadeh ................. 324/457 |
| 5,051,937 | A | 9/1991 | Kawate et al. ................. 364/571 |
| 5,986,549 | A | 11/1999 | Teodorescu .................... 340/561 |
| 6,348,862 | B1* | 2/2002 | McDonnell et al. .......... 340/561 |
| 6,768,420 | B2* | 7/2004 | McCarthy et al. ......... 340/573.1 |
| 6,900,642 | B2* | 5/2005 | Zank et al. .................... 324/457 |

FOREIGN PATENT DOCUMENTS

| GB | 2340248 A | 2/2000 |
| NZ | 209261 | 8/1984 |
| WO | WO00/52657 | 9/2000 |
| WO | WO03/050547 | 6/2003 |

OTHER PUBLICATIONS

Transducers in Mechanical and Electrical Design, 1986, Chapters 1 (pp. 1-15) and 4 (pp. 97-113).

* cited by examiner

*Primary Examiner* — Thomas Mullen

(57) ABSTRACT

A sensing system is disclosed that uses at least one conductive plate and associated electronic circuitry to provide an output that is indicative of an object's position in relation to the at least one conductive plate. The sensing system is provided with a high impedance drive signal that varies as a result of the location of an object relative to the at least one conductive plate. The electronic circuitry receives a high impedance drive signal value as an input and a processor uses the value to calculate a digital output indicative of the object's position. The high impedance drive signal value is monitored over time enabling the objects position, displacement, pressure, movement, impact and energy to be determined. This data is output to a display and may also be transmitted to a person located remotely from the object being monitored.

20 Claims, 8 Drawing Sheets

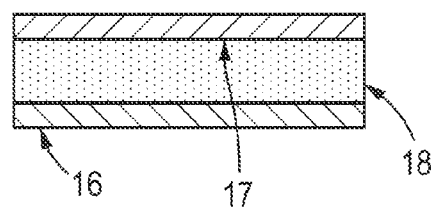
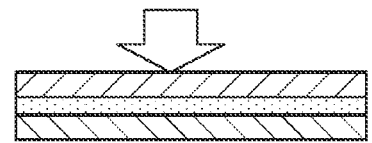
FIG.10a  FIG.10b
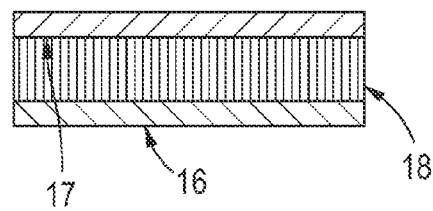
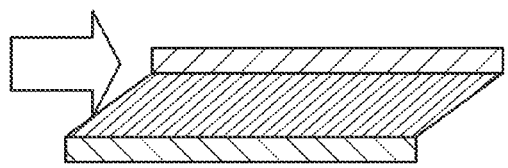
FIG.11a  FIG.11b
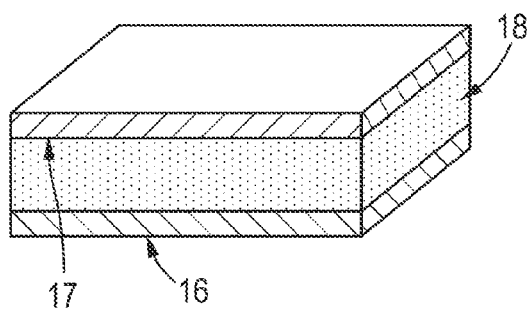
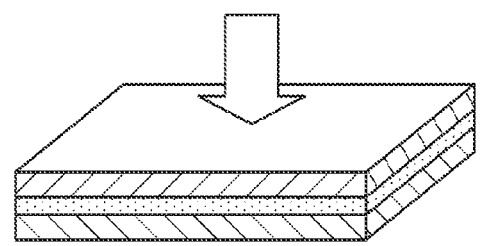
FIG.12a  FIG.12b

ELECTRIC FIELD SENSING DEVICE

CROSS-REFERENCE TO RELATED APPLICATIONS

This application is a Continuation application of U.S. patent application Ser. No. 11/791,208, filed Nov. 2, 2007, now abandoned, which is a national stage application of and claims priority to PCT/NZ05/00309, filed Nov. 22, 2005, which claims priority to New Zealand application 536,762, filed Nov. 22, 2004, which is incorporated by reference herein.

FIELD OF INVENTION

This invention relates to a contactless monitor and particularly to a conductive surface coupling an electric field between conductive bodies that provides a system capable of detecting movement, position and pressure of a body.

SUMMARY OF THE PRIOR ART

A number of systems are known in the art for providing a contactless monitor or alarm condition responsive to the activity of humans or animals. More commonly known forms of monitor or alarm are for use in a hospital environment or home which responds to respiration and apnea and more particularly its application to preventing apnea in small infants and premature babies. Respiration monitors of this type are used in hospitals providing a visible and/or aural indication of when a patient develops abnormal breathing patterns or has stopped breathing.

In U.S. Pat. No. 4,033,332 to Cavitron Corporation, a contactless activity and respiration monitor is disclosed which includes a resilient, capacitive pad (a mattress) or a pad used as a mattress, having a capacitor therein which is responsive to the activity or respiration of a patient lying on the pad. Coupled to the capacitor pad is electronic sensing circuitry and an alarm unit that provides an indication and/or alarm when abnormal respiratory rates change or when apnea occurs. This monitor is capable of responding to and distinguishing between small movements of the patient being monitored due to breathing, including apnea, and larger movements of the patient that would naturally cause the breathing rate of a patient to increase and result in false alarms being indicated. This monitor uses three layers of conductive wire mesh electrodes having foam between each layer. The sandwiched construction is then placed either within or under an infant's mattress, for example. When an infant is lying on the pad the relative motion between electrodes caused by breathing effectively changes the capacitance between the electrodes. The change in capacitance is sensed by the electronic circuitry and if the detected level falls outside a predetermined threshold level a visual and/or aural alarm is used to alert medical staff. The system uses rudimentary integrator and filtering circuits to detect long term changes of capacitance caused by increased breathing rate or apnea. One of the disadvantages of this type of system is that it cannot measure static parameters such as distance, force or pressure, it is susceptible to electrostatic pick up at mains line frequency, can only measure event changes and not constant values such as would occur when a person sits still. A further disadvantage is that the electronic circuitry responds to electrostatic charges generated by movement of the pad cable, unless non-micro phonic cabling was used and as such the circuit requires a drive conductor and a receive conductor.

SUMMARY OF THE INVENTION

It is an object of the present invention to provide a contactless monitoring system which goes some way to overcoming the abovementioned disadvantages in the prior art or which will at least provide the industry with a useful choice.

Accordingly, in a first aspect the invention consists in an electric field sensing system used to detect movement, position and pressure of an object comprising:

at least one conductive plate, a reference input signal, a high impedance drive signal input generated from said reference input signal and connected to said at least one conductive plate producing an electric field around said at least one conductive plate, a processing circuit that receives as an input said reference input signal and said high impedance drive signal, and generates a digital signal output, and wherein a position of said object in said electric field determines a value of said high impedance drive signal and said processing circuit provides said digital signal output indicative of said object's position in relation to said at least one conductive plate.

Preferably, said high impedance drive signal is also a sense signal.

Preferably, said processing circuit uses said values in said high impedance drive signal input to calculate at least one of displacement, position and pressure caused by said object.

Preferably, said processing circuit uses said values in said high impedance drive signal input over time to calculate at least one of movement, impact or energy caused by said object.

Preferably, said digital signal output is input to a display system incorporating an audible alarm.

Alternatively, said digital signal output is input to a display system.

Alternatively, said digital signal output is input to an audible alarm system.

Preferably, said digital signal output is transmitted from said electric field sensing system via at least one of a radio, mobile communications network and the internet to a person located remotely from a user of said electric field sensing system enabling said remotely located person to receive on an electronic device said digital data in real-time.

Preferably, said electronic device includes at least one of a radio, mobile telephone, personal digital assistance, internet connection device and computer.

Preferably, said at least one conductive plate is constructed from a solid material.

Alternatively, said at least one conductive plate is constructed from at least one of a flexible and stretchable material.

Preferably, said solid material is a copper plate.

Alternatively, said solid material is a carbon impregnated polyethylene pad.

Preferably, said at least one conductive plate is coated with a conductive ink such as silver.

Alternatively, said at least one conductive plate is coated with a conductive ink such as carbon.

Preferably, said flexible material is a conductive membrane.

Alternatively, said flexible material is a plurality of conductive fibres.

Preferably, said flexible material is adhered to or sewn to a garment or other section of flexible type of material which, in use, does not inhibit the ability of a user to perform a task.

In a second aspect the invention consists in a multilayered electric field sensing system used to detect at least one of movement, position and pressure of an object comprising:

a plurality of electrically coupled conductive plates forming a layered construction, a plurality of compressible insulating members interleaved with said conductive plates, a reference input signal, a high impedance drive signal input generated from said reference input signal and connected to at least one of said conductive plates producing an electric field between said layered construction, a processing circuit that receives as an input said reference input signal and said high impedance drive signal, and generates a digital signal output, and wherein a position of said object in said electric field determines a value of said high impedance drive signal and said processing circuit provides said digital signal output indicative of a position of said object in relation to said plurality of electrically coupled conductive plates.

Preferably, said high impedance drive signal is also a sense signal.

Preferably, said conductive plate layered construction is formed by at least an upper conductive plate, a lower conducive plate and a third conductive plate therebetween.

Alternatively, said conductive plate layered construction is formed by a plurality of conductive plates, said plurality of conductive plates being an odd number and there are n odd numbered conductive plates and m even numbered conductive plates.

Preferably, said upper and lower conductive plates are electrically connected to ground and said third conductive plate is connected to said high impedance drive signal.

Preferably, each of said n odd numbered conductive plates are electrically connected to ground and each of said m even numbered conductive plates are connected to said high impedance drive signal.

Preferably, said insulation layers are a compressible medium such as high density foam.

Alternatively, said insulation layers are a compressible medium such as an elastomer foam material.

Preferably, said processing circuit uses said changes in said high impedance drive signal inputs to calculate at least one of displacement, position, pressure, impact and energy caused by said object.

Preferably, said digital signal output is input to a display system incorporating an audible alarm.

Alternatively, said digital signal output is input to a display system.

Alternatively, said digital signal output is input to an audible alarm system.

Preferably, said digital signal output is transmitted from said electric field sensing system via at least one of a radio, mobile communications network and internet to a person located remotely from a user of said electric field sensing system enabling said remotely located person to receive on an electronic device said digital data in real-time.

Preferably, said electronic device includes at least one of a radio, mobile telephone, personal digital assistance, internet connected device and computer.

Preferably, said at least one conductive plate is constructed from a solid material.

Alternatively, said at least one conductive plate is constructed from at least one of a flexible and stretchable material.

Preferably, said solid material is a copper plate.

Alternatively, said solid material is a carbon impregnated polyethylene pad.

Preferably, said at least one conductive plate is coated with a conductive ink such as silver.

Alternatively, said at least one conductive plate is coated with a conductive ink such as carbon.

Preferably, said flexible material is a conductive membrane.

Alternatively, said flexible material is a plurality of conductive fibres.

Preferably, said flexible material is adhered to or sewn to a garment or other section of flexible type of material which, in use, does not inhibit the ability of a user to perform a task.

In a third aspect the invention consists in a double layer electric field sensing system used to detect movement, position and pressure of an object comprising:

an electronic circuit used to generate a multiplexed high impedance signal and a multiplexed low impedance inverted drive signal, a first conductive plate energised by said multiplexed high impedance drive signal, a second conductive plate energised by said multiplexed low impedance inverted drive signal, a compressible insulating layer located between said first and second conductive plates, a processing circuit that obtains as an input said multiplexed high impedance drive signal, calculates variations in said multiplexed high impedance drive signal and generates a digital signal output, and wherein said first conductive plate is electrically orthogonal to said second conductive plate generating a matrix of electrically coupled cells whereby a position of said object determines a number of coupling interactions between said electrically coupled cells and said processing circuit measures said positions and provides said digital signal output indicative of said object position.

Preferably, said high impedance drive signal is also a sense signal.

Preferably, said insulation layers are a compressible medium such as high density foam.

Alternatively, said insulation layers are a compressible medium such as an elastomer foam material.

Preferably, said processing circuit uses said changes in said multiplexed high impedance drive signal inputs to calculate at least one of displacement, position, pressure, movement, impact or energy caused by said conductive body.

Preferably, said digital signal output is input to a display system incorporating an audible alarm.

Alternatively, said digital signal output is input to a display system.

Alternatively, said digital signal output is input to an audible alarm system.

Preferably, said digital signal output is transmitted from said electric field sensing system via at least one of a radio, mobile communications network and the internet to a person located remotely from a user of said electric field sensing system enabling said remotely located person to receive on an electronic device said digital data in real-time.

Preferably, said electronic device includes at least one of a radio, mobile telephone, personal digital assistance, internet connected device and computer.

Preferably, said at least one conductive plate is constructed from a solid material.

Alternatively, said at least one conductive plate is constructed from at least one of a flexible and stretchable material.

Preferably, said solid material is a copper plate.

Alternatively, said solid material is a carbon impregnated polyethylene pad.

Preferably, said at least one conductive plate is coated with a conductive ink such as silver.

Alternatively, said at least one conductive plate is coated with a conductive ink such as carbon.

Preferably, said flexible material is a conductive membrane.

Alternatively, said flexible material is a plurality of conductive fibres.

Preferably, said flexible material is adhered to or sewn to a garment or other section of flexible type of material which, in use, does not inhibit the ability of a user to perform a task. In a fourth aspect the present invention consists in a method of monitoring the performance of a user incorporating any one of the conductive plate arrangements and associated sensing system circuit comprising the steps of:

placing said conductive plate arrangement and said associated sensing system in close proximity to said user, measuring changes in electrical characteristics between said conductive plates using said associated sensing system when said user moves in relation to said conductive plates, applying a plurality of algorithms to said measured changes to calculate at least one of movement parameters of displacement, force, shear force and pressure, converting said movement parameters into a digital signal output, and outputting said movement parameters to said user.

Preferably, said step of measuring said changes in electrical characteristics includes measuring fluctuations in a high impedance drive signal applied to said conductive plate arrangement as a result of said user's movement in relation to said conductive plate arrangement.

Preferably, said step of outputting said movement parameters includes inputting said digital signal output from said sensing system to a display system incorporating an audible alarm.

Alternatively, said step of outputting said movement parameters includes inputting said digital signal output from said sensing system to a display system.

Alternatively, said step of outputting said movement parameters includes inputting said digital signal output from said sensing system to an audible alarm.

Preferably, said step of outputting said movement parameters includes transmitting said digital signal output from said sensing system to a remote electronic device.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

This invention consists in the foregoing and also envisages constructions of which the following gives examples.

BRIEF DESCRIPTION OF THE DRAWINGS

Preferred forms of the present invention will now be described with reference to the accompanying drawings in which;

FIGS. 10a and 10b are side views of a layered electrically coupled conductive plate used with the second and third preferred embodiments of the present invention showing the change in distance between the conductors as a result of a force being applied to the conductors, FIGS. 11a and 11b are side views of a layered electrically coupled conductive plate used with the second and third preferred embodiments of the present invention showing the effects of a shear force being applied to the conductors, FIGS. 12a and 12b are side views of a layered electrically coupled conductive plate used with the second and third preferred embodiments of the present invention showing the effects on the conductive plates when a pressure is applied to the conductors.

DETAILED DESCRIPTION OF THE PREFERRED EMBODIMENTS

Whilst there are a number of different monitors available for detecting a human, animal or any other forms of non-insulating object movement and/or for detecting changes in respiratory rate or detecting apnea, the present invention is directed to an electric field sensing system 1 which can be utilised in a broad range of applications, such as; infant respiratory monitoring systems, pressure detection systems as a means of preventing bed sores; in wheel chairs to detect the movement of the occupant and provide a means of determining the risk of the occupant developing sores as a result of being in a sedentary position for a prolonged period of time; placing the sensor in a shoe to detect pressure while running in order to determine false leg follow-through based on early foot strike detection or alternatively the system could be used as a proximity sensor to control the sense of touch for robotic limbs. The contactless monitoring system allows static parameters such as force and pressure to be measured. As illustrated by the above examples the number and types of application to which the present invention can be directed is very broad.

Figure 1:
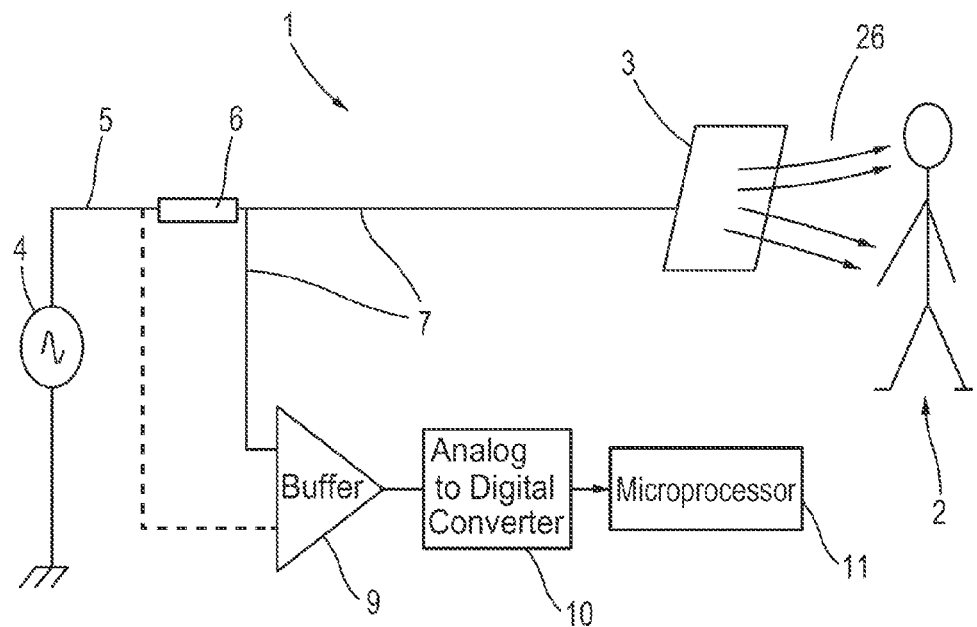
FIG. 1 is a block diagram of the electric field sensing system of the first preferred embodiment of the present invention.

Referring to FIG. 1, a first preferred embodiment of the electric field sensing system of the present invention is shown that uses a single conductive plate 3 that provides improvements over systems currently available in a number of industries and the medical or sports industries in particular. A conductive plate 3 coupled with a microprocessor based circuit is described which provides a means of measuring position and movement variations applied to the conductive plate 3 such that erroneous or false alarm detections are substantially reduced. A system of this type will provide a means of enhancing personnel safety through the provision of visual and/or audible alarms to which medical staff, for example, will react to knowing that there is a minimal risk of the alarm being false.

It will be appreciated that the electric field sensing system 1 as described in the first preferred embodiment of the present invention can be used in a broad range of applications including the medical and sports industries generally but will now be described below with reference to use in the neonatal care environment to monitor the respiratory rate of neonates and in particular for the early detection of apnea (cessation of breathing). It will be appreciated that the present invention can be applied to various applications within the hospital environment, including but not limited to a contactless electric field pad.

Electric Field Sensing Circuit

The conductive plate 3 is constructed from a conductive material such as copper or carbon impregnated polyethylene and may also be coated with conductive inks such as silver or carbon. Alternatively, the plate 3 may be constructed from a flexible material using one or a number of sandwiched membranes. The circuit which provides the signal input to drive the electric field sensing system 1 is illustrated at FIG. 1. In the first preferred embodiment, an alternating current (AC) source 4 generates a sine wave signal (reference signal) 5 of a preselected frequency. To generate a high impedance signal 7 to drive the electric field sensing system 1, the reference signal 5 is input through a high impedance resistor 6 before being applied to conductive plate 3. The reference signal 5 is also used as an input clocking signal to an analogue-to-digital converter (ADC) 10. Hence, as the reference signal 5 and ADC clock signal are in phase, synchronisation of signal peaks and troughs can be measured using the ADC 10.

An electric field 26 is generated around the conductive plate 3 being driven with the high impedance drive signal 7. When a conductive body or object 2 moves over or near the conductive plate 3, the electric field 26 between the conductive body 2 and the conductive plate 3 is altered. The movement alters the electric field coupling of the high impedance drive signal 7. Moving a conductive body or object 2 closer to the conductive plate 3 increases the coupling between the high impedance drive signal 7 and the object 2 thereby attenuating the high impedance drive signal 7. Hence, the greater the common area between the conductive plate 3 and object 2, the higher the attenuation of the high impedance drive signal 7 and the subsequent changes in electric field coupling are measured as a voltage by the processing circuitry as shown in FIG. 1. An example of changes in voltage as a result of changes in electric field coupling due to the movement of the object 2 in relation to the conductive plate 3 is shown in FIG. 2. Measuring the change in high impedance drive signal strength provides a means of measuring the distance between the conductive plate 3 and the object 2 or common area between the conductors 2, 3 to be measured. Hence, the high impedance drive signal 7 is also used as the sense signal.

Figure 2A:
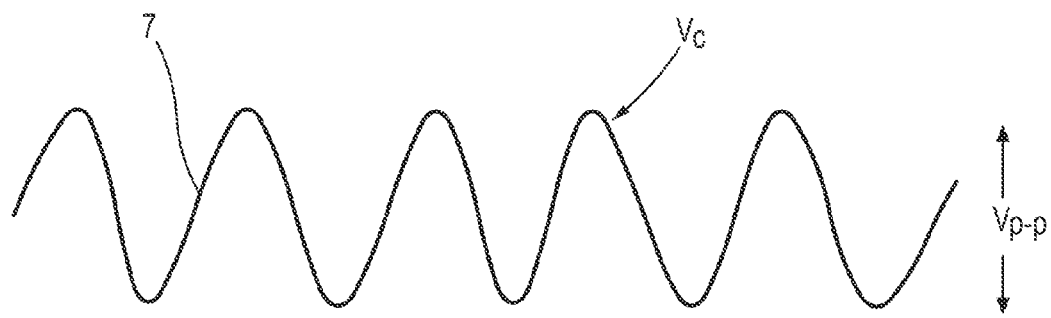
FIGS. 2a and 2b are waveform diagrams illustrating high impedance drive signal variations measured by the electric field sensing system of FIG. 1.
Figure 2B:
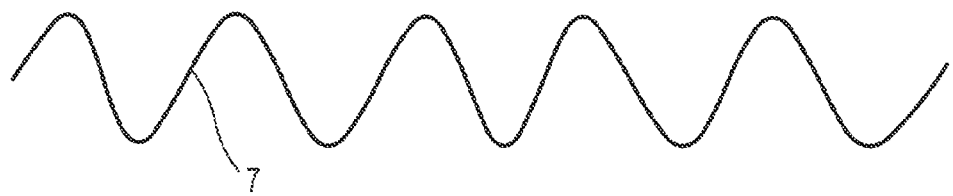

With reference to FIGS. 2a and 2b, the waveform illustrates the changes in the high impedance drive signal due to an object or conductive body 2 moving towards the conductive plate 3. FIG. 2a shows a sine wave of voltage $V_c$, having a peak-to-peak amplitude $V_{p-p}$ that corresponds to the high impedance drive signal 7 applied to the conductive plate 3 with no movement detected by the electric field sensing system 1. When the electric field sensing system 1 has an external force applied or conductive body 2 changes position, the high impedance drive signal 7 amplitude $V_{p-p}$ is reduced as a result of the electrical coupling between the conductive plate 3 in relation to the conductive body 2. The change in amplitude $V_{p-p}$ is shown in FIG. 2b. The reduction in high impedance drive signal 7 amplitude $V_{p-p}$ is measured by the processing circuitry which applies a number of algorithms to convert the signal variations into a meaningful data output to a display system and/or audible alarm system (not shown). Whilst a symmetrical sine wave alternating current is applied to the system as shown in FIG. 1, the processing circuitry is capable of performing the necessary calculations and provide a meaningful output when other symmetrical or unsymmetrical waveforms are applied.

To increase the sensitivity of the electric field sensing system 1, the reference signal 5 may be input to a difference amplifier (not shown) along with the high impedance drive signal 7. The difference between the reference signal 5 and high impedance drive signal 7 can be measured when the separation distance between conductors 2, 3 is varied thereby causing the high impedance drive signal voltage to vary as a result of the change in electric field coupling. These voltage variations are buffered 9 and input to the ADC 10 thereby converting the resultant analogue voltage into a digital data output which is input to the microprocessor 11 for further processing. The microprocessor 11 implements a number of algorithms in order to measure sensed voltage signal variations representative of movement and force or pressure variations which correspond to changes in breathing patterns, for example.

The microprocessor 11 uses a crystal clock (not shown) to clock the circuit internal digital signals and is also used as a source to drive the conductive plate or sensor plate 3. This provides an advantage over other systems as the microprocessor 11 inherently knows the frequency of the drive 5 and sense signals 7. Hence, using software programmes, the microprocessor 11 can phase lock with the sense signal 7. This allows the ADC 10 to be triggered in phase and in a frequency dependent way thereby allowing synchronous detection of changing events without the use of external devices.

Therefore, the sensing system 1 of the first preferred embodiment of the present invention is inherently frequency locked and the ADC 10 synchronously detects the time varying signal, allowing the time varying signal to be referenced to a zero frequency reference. Hence, timing variations due to changes in the timing source over time and changes in environmental conditions are naturally tracked and cancelled.

Multilayered Electric Field Sensing System

Figure 3:
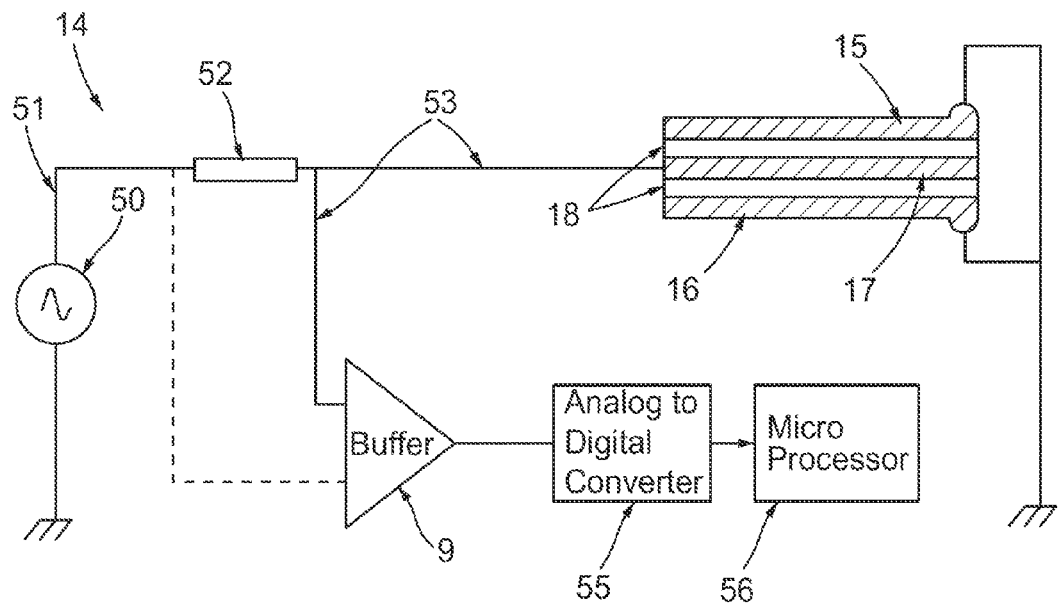
FIG. 3 is a block diagram of a second preferred embodiment of the present invention using a multilayered electric field sensing system.
Figure 4:
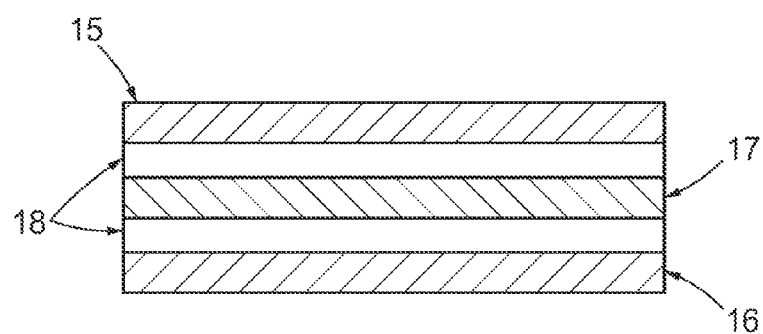
FIG. 4 is a side view of a layered electrically coupled conductive plate used with the electric field sensing system of the second embodiment of the present invention.

With reference to FIGS. 3 and 4, a second preferred embodiment of the present invention is shown which uses at least three conductive plates 15, 16, 17, having an insulating layer 18 placed between each conducting plate 15, 16, 17, forming a sandwich. The sandwiched conducting plate system coupled with a microprocessor based circuit as described in this embodiment provides a means of measuring position, movement and pressure variations applied to the sandwiched conductive plates such that erroneous or false alarm detections are substantially reduced. The use of a multilayered electric field sensing system 14 provides a means of calculating pressure variations as well as movement and position variations.

Figure 5:
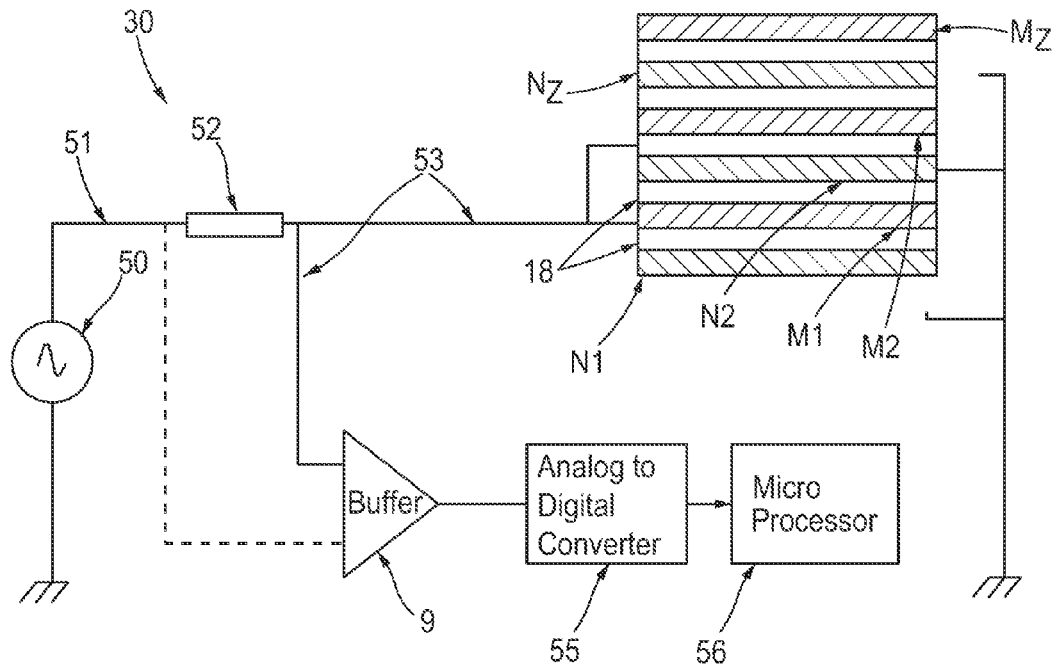
FIG. 5 is a block diagram showing a number of conductive plates as applied to the multilayered electric field sensing system of FIG. 3, FIGS. 6a and 6b illustrate a flexible conductive pad applied to the electric field sensing system of FIG. 1.

As illustrated in FIG. 5, the multilayered sandwiched conductor plate sensing system 30 need not be limited to three conductive plates. FIG. 5 shows a number of conductors N1, M1, N2, M2 ... $M_z$, $N_z$, having a compressible medium 18 between each conductor of the type provided in FIGS. 3 and 4. The conductors N1 to $N_z$ may be either solid conductors or alternatively, each of the "plates" can be a flexible conductive surface such as a membrane adhered to or sewn into material. As can be seen in FIG. 5, each alternative conductive surface (N1, N2 ... $N_z$) has been grounded while the interleaved conductive surfaces (M1, M2 ... $M_z$) are driven by the high impedance drive signal 7 enabling a sensed signal to be detected as previously detailed in the first preferred embodiments of the present invention.

Conductive Plates

FIG. 4 shows the multilayered construction of the sensing system 14 having at least three conductive plates 15, 16, 17 with insulated layers 18 between each plate forming a sandwich type construction. The insulated layers 18 are formed of a compressible material such as high impact foam or other elastomer foam. Each of the conductive plates 15, 16, 17 are of the same construction as those as described with reference to the first preferred embodiment as shown in FIG. 1. The upper and lower conductive plates 15, 16 are electrically connected to ground in order to provide a shield to isolate the sensor plate (middle conductive plate) 17 from electromagnetic interference whilst acting as coupling plates, such that movement of these plates 15, 16 causes the high impedance drive signal 7 supplied to the sensor plate 17 to vary.

Figures 6A, 6B:
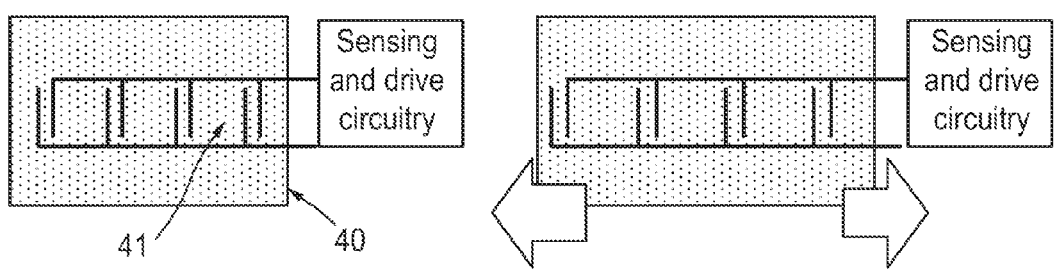

FIGS. 6a and 6b show an alternative type of conductor 40 whereby the conductor 40 is made from a stretchable medium such as a membrane sewn or adhered to material. The conductor 40 has metallic fingers 41, conductive ink or conductive fibres which are electrically connected to the drive and sensing circuitry of any of the preferred embodiments of the present invention. Hence, when the flexible conductive material 40 is stretched, as shown in FIG. 6b, the coupling changes between the metallic fingers 41 thereby causing the distance between adjacent metallic fingers 41 to vary and hence the high impedance drive signal 7 supplied to alternate fingers 41 to vary.

Multilayered Electric Sensing Circuit

A circuit that provides the signal input to drive the multilayered electric field sensing system 14 is illustrated at FIG. 3. This sensing circuit can also be applied to the multilayered electric field sensing system 30 as illustrated in FIG. 5. The sensor plate 17 is connected to an alternating current (AC) source 50 which generates a sine wave signal (reference signal) 51 from which a high impedance signal 53 to drive the sensing system 14 is generated when the reference signal 51 is input through a high impedance resistor 52 before being input to sensor plate 17. The reference signal 51 is also used as an input clocking signal to the analogue-to-digital converter (ADC) 55. Hence, as the reference signal 51 and ADC clock signal are in phase, synchronisation of signal peaks and troughs can be measured using the ADC 55.

As the sense plate 17 is sandwiched between an electrically grounded upper and lower conductive plate 15, 16, and separated by a compressive medium 18, changes in the position of the conductive plates 15, 16 either horizontally or vertically, alters the electric field coupling of the high impedance drive signal 53. Moving one or both of the conductors 15, 16 closer to the sense plate 17 increases the coupling between the high impedance drive signal 53 and the conductor 17 thereby attenuating the high impedance drive signal 53. Alternatively, moving the conductors 15, 16, 17 horizontally in relation to each other changes the common area between the conductors 15, 16, 17. This also results in a change in electric field coupling thereby changing the high impedance drive signal 53. Hence, the greater the common area between conductors 15, 16, 17, the higher the attenuation of the high impedance drive signal 53. The subsequent changes in electric field coupling are measured as a voltage by the processing circuitry 56. Measuring the change in high impedance drive signal strength provides a means of measuring the distance between two conductors or common area between conductors to be measured.

The sensitivity of the multilayered electric field sensing system 14 can be increased in the manner already described with reference to FIG. 3 using a difference amplifier (not shown) along with the high impedance drive signal 53.

Matrix System Circuit

Figure 7:
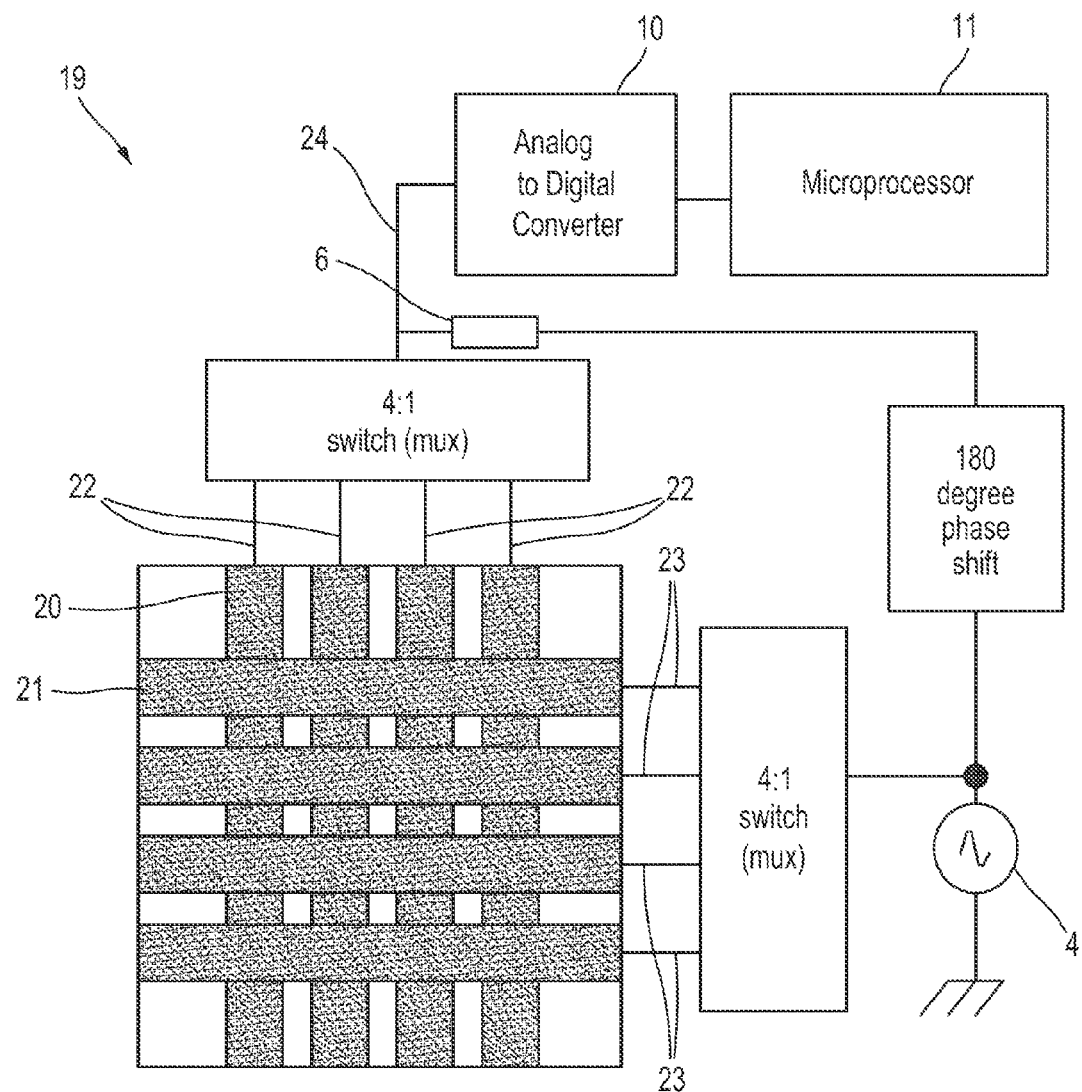
FIG. 7 is a block diagram of a third preferred embodiment of the present invention utilising a double layer electric field sensing system.

A third preferred embodiment of the present invention is shown in FIG. 7. A multiplexed electric field sensing system 19 is provided using two conductive plates 20, 21 separated by a compressible medium 18 of the type described with reference to FIGS. 3 and 5. A matrix of cells is generated using orthogonal drive signals in conjunction with multiplexed or switched electric fields. The lower conductor (rows) 21 is driven with a multiplexed high impedance drive signal 23 and the upper conductor (columns) 20, an electrically orthogonal conductive plate, is electrically grounded or driven with a multiplexed low impedance inverted drive signal 22. Hence, where the upper and lower conductors 20, 21 electrically overlap, changes in distance between the two conductors 20, 21 causes a change in the amplitude and phase of the high impedance drive signal 24 between the conductive plates 20, 21. This change in high impedance drive signal 24 is converted from an analogue signal to digital data via the ADC 10 and provided as an input to the microprocessor 11. By selectively driving different orthogonal conductors in the matrix, each cell in the matrix may be measured and position and movement within the matrix can be determined. Furthermore, multiplexing several drive signals in time with multiple orthogonal receiving signals enables an X-Y resolution of force on the conductive plates 20 and 21 to be determined.

Figure 8:
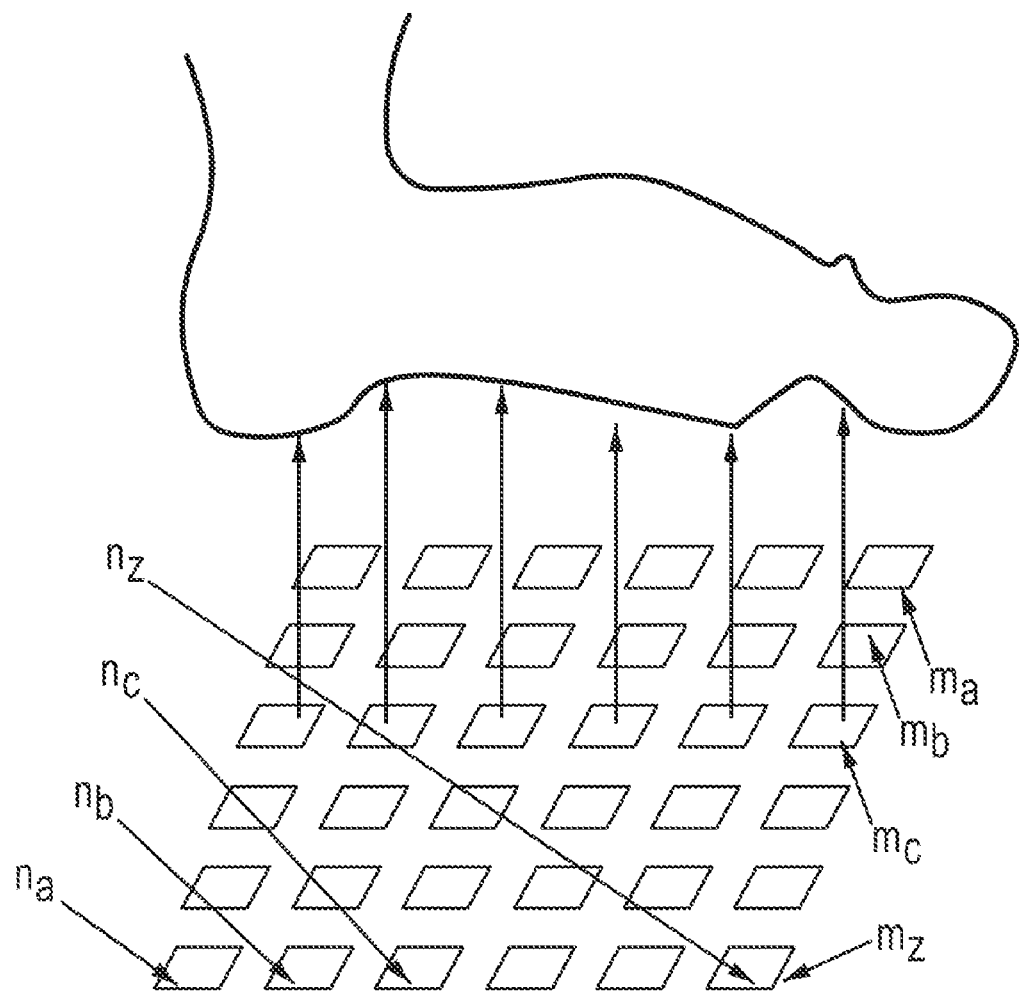
FIG. 8 is a side view of an N×M flexible sensing pad for insertion into a shoe using the electric field sensing system of FIG. 1.

Pressure and force measurements can be used to determine a person's gait. The measured data can be used as a feedback mechanism for control loops. These loops can control various pressure plates within a person's shoe, the follow-through of an artificial leg or control the dispensing of medicine. FIG. 8 shows an n×m matrix sensing pad whereby a sensing pad is inserted into a user's shoe which is made up using a number of conductive plates or flexible membranes, (na, nb, nc, ... nz)×(ma, mb, mc, ... mz), adhered to the shoe inner. This plate system operates in the same manner as the matrix sensing system as described above and is capable of sensing events in three dimensions.

Data Display

Figure 9:
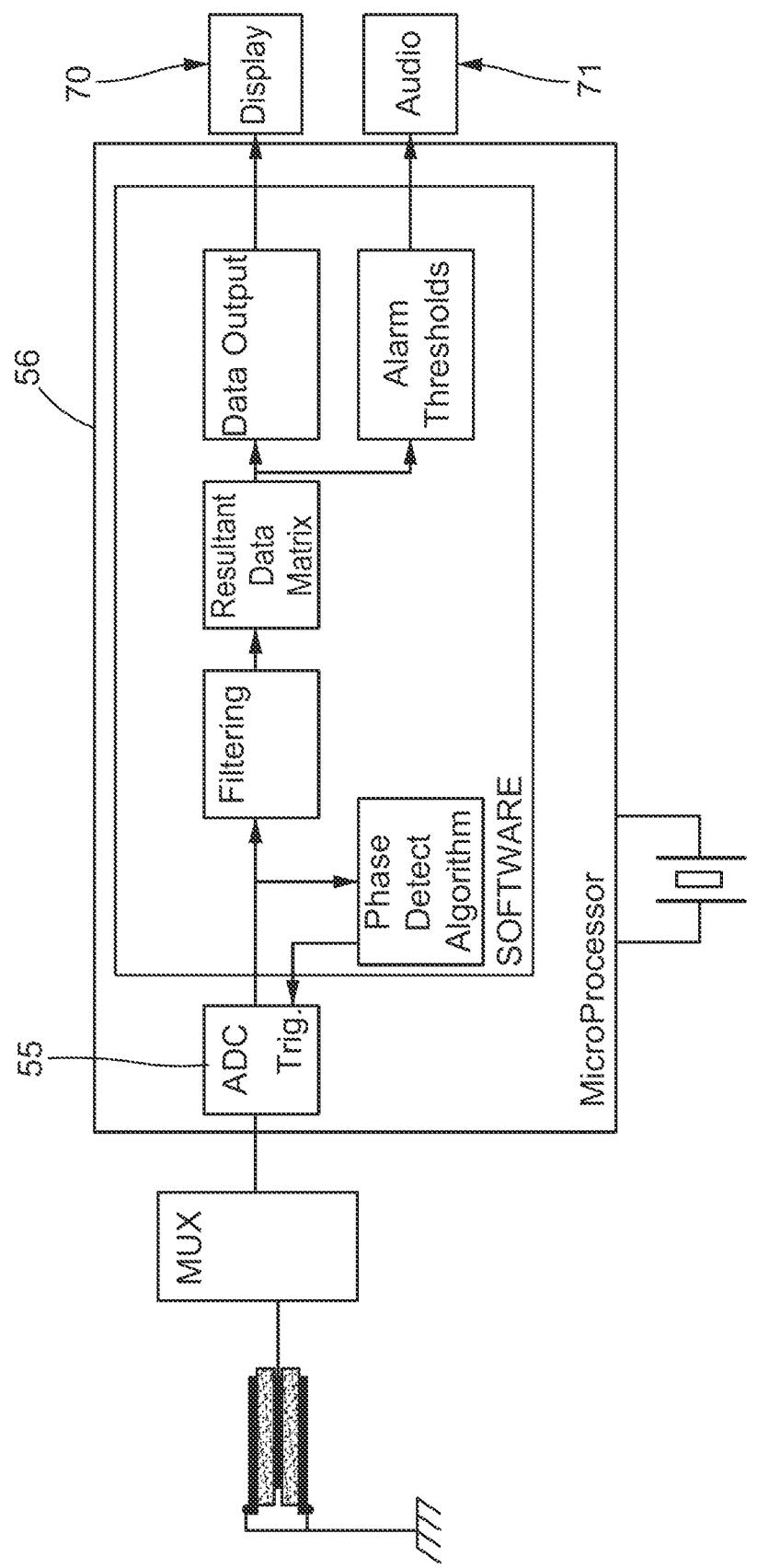
FIG. 9 is a block diagram of a digital system capable of providing an aural and visual output to a user that can be applied to any of the preferred embodiments of the present invention.

The calculated data can be output via an RS232 port (not shown) or other known connection ports, to a display system 70 providing a map illustrating the pressure difference, for example, being applied to the electric field sensing system 1, 14, 19, 30 as shown in FIG. 9. Alternatively, the display system 70 may provide a user, suchc as medical personnel, with a numerical readout of pressure, force or movement variations as a result of changes in the electric field sensing system 1, 14, 19, 30. An audible alarm 71 can also be generated providing an aural warning that a patient has been sedentary for an extended duration, or that breathing has ceased for example.

Calculations

As mentioned previously, the microprocessor 11 applies a number of software algorithms to determine pressure, force, displacement and types of forces applied to and sensed by the conductive plates for each of the embodiments of the present invention. FIGS. 10a to 12b illustrate the types of forces on conductor plates 16 and 17 and compressible material 18 that can be detected and measured. FIGS. 10*a* and 10*b* shows a force being applied to the upper conductive plate 17. Hence, by way of example, with the multilayered electric field sensing system 14 as shown in FIG. 3, as the drive signal frequency and amplitude remain constant, then knowing the force constant and density of the compressible medium 18, the derived force can be determined by multiplying the displacement of conductive plates 15, 16, 7 by the compressible medium force constant. FIGS. 11*a* and 11*b* show the effects of a shear force being applied to the electric field sensing system 14. The electrical coupling between the plates 16 and 17 can be proportional to the shear forces as well as the orthogonal forces applied to the plates 16, 17 enabling shear force to be determined. Also, knowing the area of the sensor plate 17, the pressure can also be calculated by dividing the calculated force by the sensor plate area. The effects on the conductive plates when a pressure is applied to the conductors are illustrated in FIGS. 12*a* and 12*b*. Other events that may be measured are listed below:

a. Energy which is calculated based on force applied over time.

b. Impact can be calculated based on a determination of the energy applied over time and the speed of changes of force applied to the system.

c. Breathing, diaphragm expansion and heart rate can be calculated based on the expected frequency content of each of these events and the displacement caused by the sensor system.

d. Activity based events such as seating position, walking or running gait, kicking a ball or swing a golf club for example, can be determined by adding several of the sensed events over time.

It would also be possible to determine for example, a mode of transport or type of physical activity by combining the electric field sensing system 14 with tilt and vibration sensors (not shown). Whilst other more complex calculations are undertaken by the microprocessor 11, details of these algorithms go beyond the scope of the object of the present invention and are therefore not disclosed.

Communications

Figure 13:
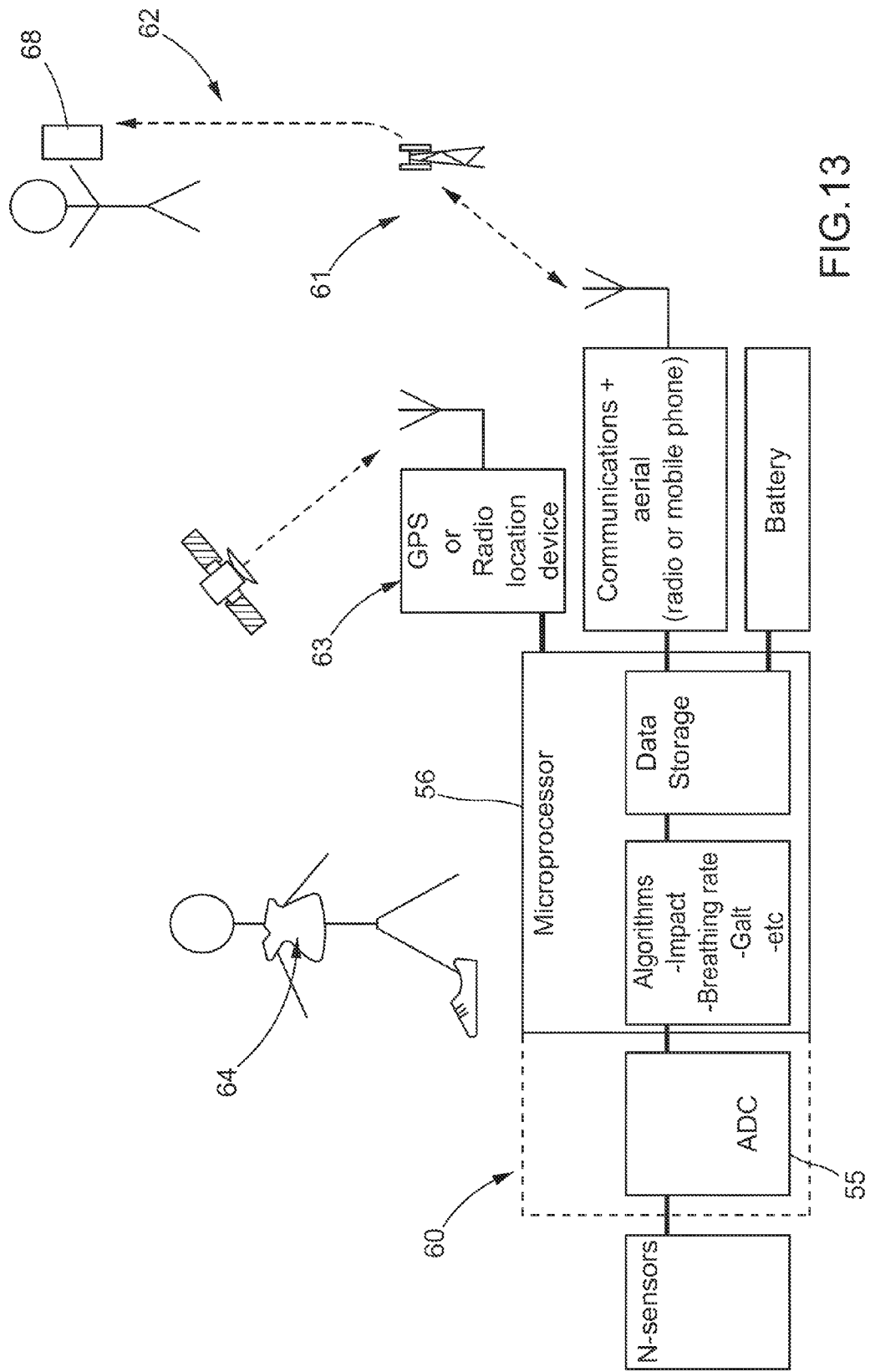
FIG. 13 is a block diagram of a circuit attached to any one of the preferred embodiments of the present invention enabling the data output from the sensing system to be transmitted to a person located remotely from a user.

The sensing and processing circuit of each of the preferred embodiments of the present invention can be modified to incorporate the output of sense data to a communications device as shown in FIG. 13. The incorporation of a communications device will provide a means of remotely sensing a physical state or method of activity in a sports event, for example. Hence, data can be output to a coach, medical practitioner or other person monitoring the sensed data via a radio, mobile telephone network 61 or alternatively via the Internet. The data is sent over the radio or mobile phone link 62 to the remote person's radio, mobile phone, personal digital assistant (PDA), Internet connected device, computer or other electronic device 68 capable of receiving radio, Internet and/or mobile phone type signals. Hence, real-time feedback can be obtained by an athlete's coach, a doctor or other person monitoring the sensing system 60. Hence, medical compliance and the characteristics of potential medical problems can be logged and transmitted enabling medical personnel, for example, to monitor a person and enable prognosis and/or diagnosis to be undertaken as soon as a problem arises.

Furthermore, a user's position along with sensed data 60 may also be monitored remotely by adding GPS circuitry 63 at the output of the sensing circuit 60. This type of data would be of great benefit to personnel involved in a search and rescue type of situation particularly if the sensing system user 64 is in difficulty and is known to be a diabetic for example, and as such, the risk of the user going into a coma is greatly reduced.

The invention claimed is:

1. An electric field sensing system used to detect movement, position and pressure of an object comprising:
   at least one conductive plate,
   a reference input signal,
   a high impedance drive signal generated from said reference input signal and connected to said at least one conductive plate producing an electric field around said at least one conductive plate,
   a processing circuit that synchronously detects and receives as an input said reference input signal and said high impedance drive signal and applies at least one algorithm to measure any variations in said high impedance drive signal, and generates a digital signal output, and
   wherein a position of said object in said electric field determines a value of said high impedance drive signal and said processing circuit provides said digital signal output indicative of said object's position or movement in relation to said at least one conductive plate.

2. The electric field sensing system according to claim 1 wherein said high impedance drive signal is also a sense signal.

3. The electric field sensing system according to claim 1 wherein said processing circuit uses said values in said high impedance drive signal to calculate at least one of displacement, position and pressure caused by said object.

4. The electric field sensing system according to claim 1 wherein said processing circuit uses said values in said high impedance drive signal input over time to calculate at least one of a movement, impact or energy caused by said object.

5. The electric field sensing system according to claim 1 wherein said digital signal output is input to a display system incorporating an audible alarm system.

6. The electric field sensing system according to claim 1 wherein said digital signal output is input to a display system.

7. The electric field sensing system according to claim 1 wherein said digital signal output is input to an audible alarm system.

8. The electric field sensing system according to claim 1 wherein said digital signal output is transmitted from said electric field sensing system via at least one of a radio, mobile communications network or the Internet to a person located remotely from a user of said electric field sensing system enabling said remotely located person to receive on an electronic device said digital signal output in real-time.

9. The electric field sensing system according to claim 8 wherein said electronic device includes at least one of a radio, mobile telephone, personal digital assistant, Internet connected device and computer.

10. The electric field sensing system according to claim 1 wherein said at least one conductive plate is constructed from a solid material.

11. The electric field sensing system according to claim 10 wherein said solid material is a copper plate.

12. The electric field sensing system according to claim 10 wherein said solid material is a carbon impregnated polyethylene pad.

13. The electric field sensing system according to claim 1 wherein said at least one conductive plate is coated with a conductive ink comprising silver.

14. The electric field sensing system according to claim 1 wherein said at least one conductive plate is coated with a conductive ink comprising carbon.

15. The electric field sensing system according to claim 1 wherein said at least one conductive plate is constructed from at least one of a flexible and stretchable material.

16. The electric field sensing system according to claim 15 wherein said flexible material is a conductive membrane.

17. The electric field sensing system according to claim 15 wherein said flexible material is a plurality of conductive fibers.

18. The electric field sensing system according to claim 15 wherein said flexible material is adhered to or sewn to a garment.

19. A multilayered electric field sensing system used to detect at least one of movement, position and pressure of an object comprising:

a plurality of electrically coupled conductive plates, a plurality of compressible insulating members interleaved with said conductive plates, a reference input signal, a high impedance drive signal generated from said reference input signal and connected to at least one of said conductive plates producing an electric field between said conductive plates, a processing circuit that synchronously detects and receives as an input said reference input signal and said high impedance drive signal and applies at least one algorithm to measure any variations in said high impedance drive signal, and generates a digital signal output, and wherein a position of said object in said electric field determines a value of said high impedance drive signal and said processing circuit provides said digital signal output indicative of a position of said object or a movement of said object in relation to said plurality of electrically coupled conductive plates.

20. The multilayered electric field sensing system according to claim 19 wherein said high impedance drive signal is a sense signal.

* * * * *